United States Patent
Tan et al.

(10) Patent No.: US 10,517,313 B2
(45) Date of Patent: Dec. 31, 2019

(54) COFFEE ROASTING APPARATUS, COFFEE BREWING APPARATUS AND COFFEE ROASTING METHOD

(71) Applicant: KONINKLIJKE PHILIPS N.V., Eindhoven (NL)

(72) Inventors: Jingwei Tan, Eindhoven (NL); Jun Zhou, Eindhoven (NL); Declan Patrick Kelly, Eindhoven (NL); Yanyan Wang, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/501,000

(22) PCT Filed: Jul. 30, 2015

(86) PCT No.: PCT/EP2015/067556
§ 371 (c)(1),
(2) Date: Feb. 1, 2017

(87) PCT Pub. No.: WO2016/020266
PCT Pub. Date: Feb. 11, 2016

(65) Prior Publication Data
US 2017/0215451 A1    Aug. 3, 2017

(30) Foreign Application Priority Data

Aug. 5, 2014 (WO) ............... PCT/CN2014/083755
Oct. 22, 2014 (EP) ................................. 14189855

(51) Int. Cl.
*A23F 5/04* (2006.01)
*G01N 21/75* (2006.01)
(Continued)

(52) U.S. Cl.
CPC .............. *A23F 5/04* (2013.01); *A47J 31/42* (2013.01); *A47J 31/4403* (2013.01);
(Continued)

(58) Field of Classification Search
CPC .. A23F 5/04; A23F 5/043; A23F 5/046; A23F 5/00; A23F 5/02; A47J 31/42;
(Continued)

(56) References Cited

U.S. PATENT DOCUMENTS 4,325,191 A * 4/1982 Kumagai ............... A23N 12/12
34/571
4,494,314 A * 1/1985 Gell, Jr. ................. A23N 12/08
219/502

(Continued)

FOREIGN PATENT DOCUMENTS

CN    101517320 A    8/2009
EP    2444734 A2    4/2012
(Continued)

OTHER PUBLICATIONS

1. Agtron Coffee Roast Analysers (http://www.agtron.net/Coffeel.html).

(Continued)

*Primary Examiner* — Drew E Becker
*Assistant Examiner* — Bryan Kim
(74) *Attorney, Agent, or Firm* — Schott, P.C.

(57) ABSTRACT

A coffee roasting apparatus including a compartment for holding coffee beans; a roasting element for roasting the coffee beans in the compartment; and a controller for controlling the roasting element. The controller is configured to control the roasting element as a function of a rate of change in the volume of the coffee beans residing in the compartment.

13 Claims, 7 Drawing Sheets

(51) Int. Cl.
  *G01N 29/00* (2006.01)
  *G01N 21/00* (2006.01)
  *A47J 31/42* (2006.01)
  *A47J 31/44* (2006.01)
  *A47J 37/06* (2006.01)
  *A23L 5/10* (2016.01)
  *A47J 37/04* (2006.01)
  *G01F 17/00* (2006.01)

(52) U.S. Cl.
  CPC .............. *G01N 21/00* (2013.01); *G01N 21/75* (2013.01); *G01N 29/00* (2013.01); *A23L 5/10* (2016.08); *A23L 5/15* (2016.08); *A23L 5/17* (2016.08); *A47J 37/04* (2013.01); *A47J 37/06* (2013.01); *G01F 17/00* (2013.01)

(58) Field of Classification Search
  CPC ........ A47J 31/44; A47J 31/4403; A47J 37/06; A47J 37/0623; A47J 37/0629; A47J 37/0635; A47J 37/0641; A47J 37/0647; A23L 5/10; A23L 5/15; A23L 5/17; A23L 7/161; A23L 7/174; A23L 7/178; A23L 7/183; A23L 7/187; A21D 6/00; A21D 6/003; A21D 8/00; A21D 8/02; A21D 8/06; A21C 13/00; A21C 13/02; G01F 17/00; G01N 21/00; G01N 21/75; G01N 29/00
  USPC .......... 426/231–233, 520, 523, 62, 241–243, 426/445, 446, 465, 466, 496, 498; 99/286, 288, 325–328, 323.4, 323.5, 99/323.7, 329 R, 331–333, 348, 468, 483
  See application file for complete search history.

(56) References Cited

U.S. PATENT DOCUMENTS

| | | | | |
|---|---|---|---|---|
| 4,501,761 A | * | 2/1985 | Mahlmann | A23F 5/046 426/467 |
| 5,373,145 A | * | 12/1994 | Endo | H05B 6/6411 219/417 |
| 5,558,797 A | * | 9/1996 | Takagi | H05B 6/6411 219/705 |
| 6,098,526 A | * | 8/2000 | Stein | G07F 17/0078 99/323.7 |
| 7,875,833 B2 | * | 1/2011 | Song | A23N 12/125 219/389 |
| 9,545,169 B2 | * | 1/2017 | Stordy | A23F 5/02 |
| 2005/0271777 A1 | * | 12/2005 | Orsini | A23F 5/04 426/281 |
| 2006/0266229 A1 | * | 11/2006 | Ribich | A23N 12/12 99/486 |
| 2009/0220645 A1 | * | 9/2009 | Martinez | A23F 5/02 426/45 |
| 2012/0265364 A1 | * | 10/2012 | Zambrano | A23F 5/04 700/300 |
| 2013/0142923 A1 | * | 6/2013 | Torres | H05B 6/705 426/233 |
| 2013/0180406 A1 | * | 7/2013 | Hay | A23F 5/04 99/286 |
| 2013/0276637 A1 | | 10/2013 | Stordy | |
| 2014/0017354 A1 | * | 1/2014 | Joseph | C12C 7/04 426/16 |
| 2014/0242239 A1 | * | 8/2014 | Boggavarapu | A23F 5/26 426/433 |
| 2014/0272023 A1 | * | 9/2014 | Zimmerman | A47J 31/56 426/231 |
| 2015/0024105 A1 | * | 1/2015 | Perlman | A23F 5/04 426/548 |
| 2015/0330640 A1 | * | 11/2015 | Stork genannt Wersborg | F24C 7/08 99/332 |

FOREIGN PATENT DOCUMENTS

| | | |
|---|---|---|
| GB | 2485073 A | 5/2012 |
| JP | S58-190350 A | 11/1983 |
| JP | 2001201057 A | 7/2001 |
| JP | 2009-542224 A | 12/2009 |
| WO | 2007142493 A1 | 12/2007 |
| WO | 2008003054 A2 | 1/2008 |
| WO | 2008123775 A1 | 10/2008 |
| WO | 2014043652 A1 | 3/2014 |

OTHER PUBLICATIONS

Office Action issued in connection with corresponding 201580041730.9, dated Nov. 15, 2018, 10 pages.

* cited by examiner

COFFEE ROASTING APPARATUS, COFFEE BREWING APPARATUS AND COFFEE ROASTING METHOD

This application is the U.S. National Phase application under 35 U.S.C. § 371 of International Application No. PCT/EP2015/067556, filed on Jul. 30, 2015, which claims the benefit of International Application No. PCT/CN2014/083755 filed on Aug. 5, 2014 and International Application No. 14189855.1 filed on Oct. 22, 2014. These applications are hereby incorporated by reference herein.

FIELD OF THE INVENTION

The present invention relates to a coffee roasting apparatus comprising a compartment for holding coffee beans; a roasting element for roasting the coffee beans in said compartment; and a controller for controlling the roasting element.

The present invention further relates to a coffee brewing apparatus comprising such a coffee roasting apparatus.

The present invention yet further relates to a method of roasting coffee beans, the method comprising heating the coffee beans to roast the coffee beans.

BACKGROUND OF THE INVENTION

Coffee has become one of the most popular beverages in modern society, with many different types and flavours of coffee being routinely available to a consumer, either in outlets such as coffee shops or in supermarkets for domestic use. The evolution of the popularity of coffee as a beverage has caused a shift in how coffee is being consumed, for instance in domestic settings.

Whereas in the past coffee would be predominantly brewed from instant coffee granules or from packaged ground coffee powders, e.g. using domestic coffee makers such as espresso machines or filter machines, nowadays a greater emphasis is placed on the freshness of the brewed coffee, which has triggered a rise in popularity of coffee roasting apparatuses. In such an apparatus, fresh, i.e. green, coffee beans can be roasted by a thermal process, e.g. using hot gases or by physical contact with a hot surface. During roasting at temperatures above 170° C., drying takes place, water is redistributed, and complex chemical reactions such as Maillard reaction and pyrolysis are induced. A fresh coffee powder can then be formed by grinding the freshly roasted coffee beans, thereby facilitating the brewing of fresh coffee. Such coffee is typically considered to have a superior taste compared to coffee brewed from packaged ground coffee powders.

The control of such a coffee roasting process is however far from trivial. Different users may require a different degree of roasting, e.g. a light roast or dark roast, of the coffee beans to cater for their personal taste. Moreover, different varieties of coffee beans will require different roasting times in order to achieve a certain roasting degree. Indeed, even different harvests of the same variety of coffee beans may exhibit variability in the required roasting times to achieve the desired degree of roasting. Therefore, one of the major challenges in providing a coffee roasting apparatus is to ensure that the roasted product meets customer expectation; e.g. has the desired degree of roasting.

Existing coffee roasting apparatuses such as the Nesco® Model CR-1000 Series of coffee roasters allow the user to specify the roasting time of the coffee beans in order to achieve the desired roasting result. Other roasting apparatuses offer control over the roasting process by allowing the user to specify the roasting temperature. However, as indicated above, it has been found that the desired roasting degree cannot be consistently achieved by (only) controlling the roasting time and/or temperature.

SUMMARY OF THE INVENTION

The present invention seeks to provide a coffee roasting apparatus that may produce roasted coffee beans in a more consistent manner.

The present invention further seeks to provide a coffee brewing apparatus comprising such a coffee roasting apparatus.

The present invention yet further seeks to provide a method of roasting coffee beans in a more consistent manner.

According to an aspect, there is provided a coffee roasting apparatus comprising a compartment for holding coffee beans; a roasting element for roasting the coffee beans in said compartment; and a controller for controlling the roasting element, wherein the controller is adapted to control the roasting element as a function of a change in the volume of the coffee beans residing in the compartment, wherein the controller is adapted to control the roasting element (140) in response to said change of volume exceeding a predefined threshold, said defined threshold indicating first cracking of said coffee beans.

The inventors have realized that in a coffee roasting process the variability in the time required to achieve the desired level of roasting is related to the variability in the time of first cracking of the coffee beans. This first cracking occurs as a result of heat-induced changes to the coffee bean structure including pore formation within the coffee bean, which is associated with a significant increase in the volume of the coffee bean. After first cracking, the further roasting of the coffee bean has been found to be highly predictable using simple mathematical models. Therefore, by directly or indirectly monitoring the significant volume changes associated with the first cracking of the coffee beans, improved control over the reproducibility of the coffee roasting process within the coffee roasting apparatus of the present invention is achieved.

The controller may be adapted to control the roasting element in response to a monitored rate of change of volume as (a change in) the rate of change of volume can be particularly indicative of the occurrence of first cracking.

Specifically, the controller may be adapted to control the roasting element in response to an increase in the monitored rate of change of volume indicative of the start of first cracking of the coffee beans; and/or a decrease in the monitored rate of change of volume indicative of the completion of first cracking of the coffee beans.

In an embodiment, the coffee roasting apparatus further comprises a sensor arrangement for determining an unoccupied volume of the compartment, wherein the controller is adapted to control the roasting element in response to the sensor arrangement. As the overall compartment volume is constant, any change (reduction) in the head space over the coffee beans in the compartment can therefore be directly associated with an increase in the volume of the coffee beans in the compartment.

To this end, the sensor arrangement may comprise a sensor adapted to transmit a signal into the compartment towards said coffee beans and to detect a reflection of said signal. From the detected reflection, a time-of-flight of the signal for instance may be derived, which can be translated into a distance the signal has travelled through the compartment, which distance is a measure of the aforementioned head space. Such a signal for instance may be an optical signal or an acoustic signal.

The sensor arrangement may be adapted to determine an initial volume occupied by said coffee beans and to monitor a change in said initial volume to facilitate detection of the first cracking phase of the coffee beans during roasting. This for instance may be achieved by monitoring changes in the time-of-flight of the signal or by transmitting a plurality of signals at different height levels of the compartment and monitoring which of the transmitted signals can travel (horizontally) across the compartment, i.e. which signals are not blocked by the coffee bean level in the compartment. In this embodiment, changes in the coffee bean level will be detected by a different (smaller) number of signals being able to travel across the compartment.

Once the first cracking stage has been identified by monitoring the volumetric changes in the coffee beans, the remainder of the roasting process may be controlled by monitoring volumetric changes or by alternative methods.

In an example embodiment, the controller may be adapted to enable the roasting element for a predefined time period upon said change in volume reaching a predefined value. In another example embodiment, the coffee roasting apparatus may further comprise a further sensor arrangement for detecting a weight and/or colour change in the coffee beans, wherein the controller is adapted to control the roasting element as a function of said change in the volume and said weight and/or colour change. This may under certain conditions improve the control over the roasting process as the volume changes in the coffee beans upon completion of the first cracking phase of the roasting process are more modest, such that these volume changed may be difficult to accurately detect, for instance if the coffee roasting apparatus contains a small amount of coffee beans only.

The coffee roasting apparatus may further comprise a user interface for defining a degree of roasting of the coffee beans, the controller being responsive to the user interface. This allows a user of the coffee roasting apparatus to precisely define the desired degree of roasting of the coffee beans.

In an embodiment, the coffee roasting apparatus may further comprise a data storage element for storing a measured change in an unoccupied volume in the compartment as a function of time to define a roasting profile of a type of coffee beans, wherein the controller is adapted to program said data storage element. Such a roasting profile may be relied upon during subsequent use of the coffee roasting apparatus with the same type of coffee beans, e.g. to improve the roasting process of the beans. For instance, the controller may be adapted to control the roasting element in accordance with the stored roasting profile in response to a user defining a degree of roasting for said type of coffee beans. This ensures that the beans are exposed to an optimized roasting profile, thereby improving the quality of the roast.

In an embodiment, the controller may be adapted to disable the roasting element upon the change in volume exceeding a defined threshold. As the change in volume can be directly correlated to the degree of roasting, such automatic disabling prevents the coffee beans from being too darkly roasted.

The coffee roasting apparatus may further comprise a data communication device for communicating detected volume change data to a remote device. This for instance facilitates the collection of roasting data from various coffee roasting apparatuses, which can be used to develop more accurate (averaged) coffee roasting profiles for different types of coffee beans.

In an embodiment, the compartment comprises an inlet; and the roasting element comprises a hot air source coupled to said inlet; the coffee roasting apparatus further comprising a stirring element mounted in said compartment for stirring the coffee beans during the roasting process. Such a hot air roasting process has been found particularly effective when combined with the volumetric change detection principle of the present invention.

In accordance with another aspect, there is provided a coffee brewing apparatus including the coffee roasting apparatus according to one or more of the aforementioned embodiments. Such a coffee brewing apparatus benefits from the improved consistency of the coffee roasting apparatus, thereby providing a coffee brewing apparatus that can brew coffee with an improved consistency in taste.

According to yet another aspect, there is provided a method of roasting coffee beans, the method comprising heating the coffee beans to roast the coffee beans; monitoring a volume change of the coffee beans during said heating; and terminating said heating in response to said volume change exceeding a defined threshold, said defined threshold indicating first cracking of said coffee beans. Such a roasting method is capable of producing roasted coffee beans in a particularly consistent manner, providing excellent control over the level of roasting of the coffee beans.

Monitoring a volume change of the coffee beans during said heating may comprises monitoring a rate of change of said volume.

Specifically, monitoring a rate of change of said volume may comprise monitoring an increase in the monitored rate of change of volume indicative of the start of first cracking of the coffee beans; and/or monitoring a decrease in the monitored rate of change of volume indicative of the completion of first cracking of the coffee beans.

Terminating said heating in response to said volume change exceeding a defined threshold may comprise terminating said heating after a predefined period of time upon said volume change exceeding the defined threshold in order to complete the coffee bean roasting process in a consistent manner.

BRIEF DESCRIPTION OF THE DRAWINGS

Embodiments of the invention are described in more detail and by way of non-limiting examples with reference to the accompanying drawings, wherein.

DETAILED DESCRIPTION OF EMBODIMENTS

It should be understood that the Figures are merely schematic and are not drawn to scale. It should also be understood that the same reference numerals are used throughout the Figures to indicate the same or similar parts.

Figure 1:
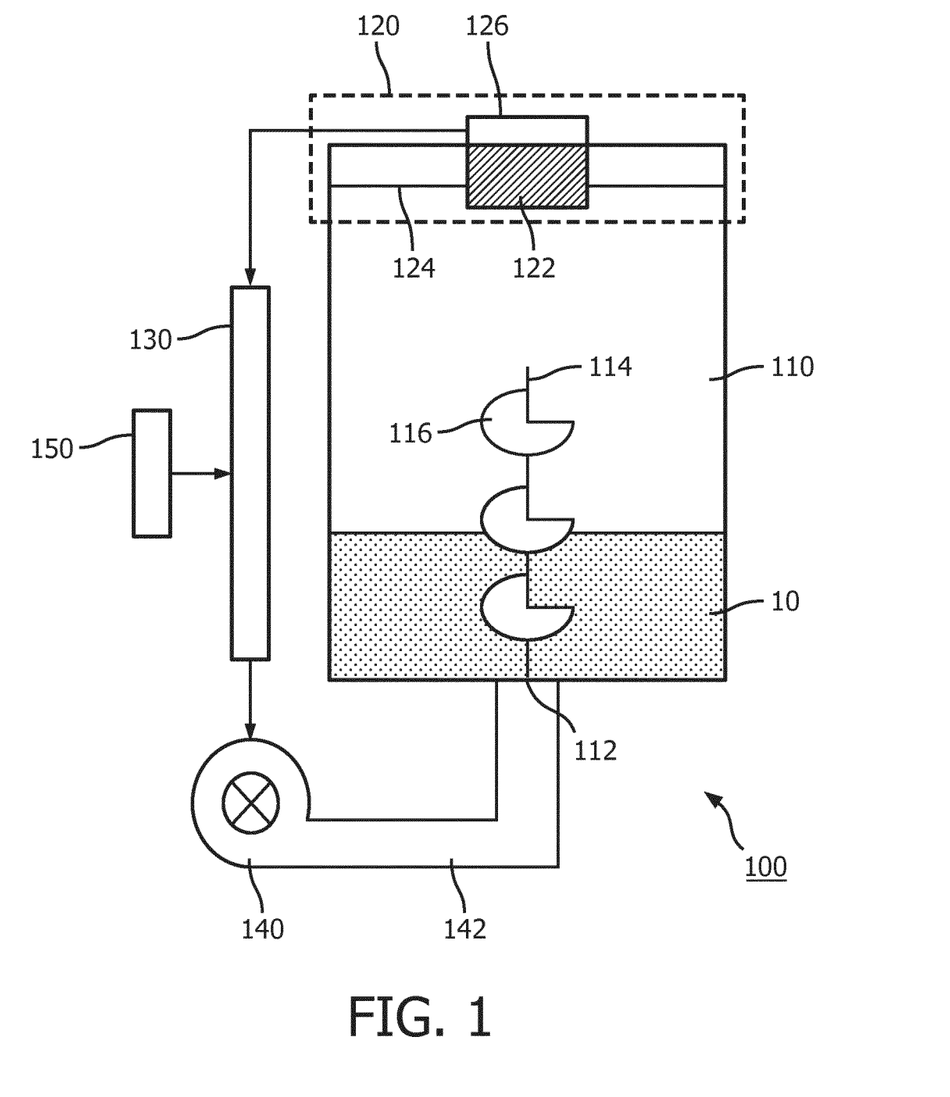
FIG. 1 schematically depicts a coffee roasting apparatus according to an embodiment.

FIG. 1 schematically depicts a coffee roasting apparatus 100 according to an embodiment. The coffee roasting apparatus 100 typically comprises a compartment 110 for storing coffee beans 10 therein. The compartment 110 may further comprise a stirring arrangement including stirring members, e.g. agitating blades, 116 mounted on or otherwise affixed to a stirring bar 114 to stir the coffee beans 10 during the roasting process of the coffee beans. This stirring arrangement assists in ensuring a homogeneous roasting of the coffee beans 10 in the compartment 110. The stirring arrangement may be controlled in any suitable manner, for instance by a controller 130, which will be explained in further detail below.

The coffee roasting apparatus 100 typically further comprises a heating arrangement for heating the coffee beans 10 during the roasting process. In an embodiment, the heating arrangement may be controlled by the controller 130. The heating arrangement ensures that the coffee beans 10 are heated to an appropriate temperature at which the roasting of the coffee beans 10 takes place, i.e. an appropriate temperature at which the desired chemical reactions such as the Maillard reaction and pyrolytic reactions take place. In FIG. 1, the heating arrangement is embodied by a hot air generator 140 connected to an inlet 112 of the compartment 110 via a conduit 142 by way of non-limiting example only. In this embodiment, the inlet 112 is typically arranged such that the hot air is guided through the coffee beans 10 during the roasting process, e.g. when stirring the coffee beans 10 using the stirring arrangement. The inlet 112 may comprise a fine grid or the like to prevent coffee beans 10 from entering the conduit 142.

However, it should be understood that any suitable heating arrangement for heating the coffee beans 10 may be used, such as one or more heating elements attached to or integrated into the one or more walls of the compartment 110, in which case the inlet 112 may be omitted. As such heating arrangements are well-known per se, they will not be explained in further detail for the sake of brevity only.

The controller 130 is adapted to control the heating arrangement at least partially in response to a change in the volume of the coffee beans 10 residing in the compartment 110 during the roasting process. In an embodiment, in order to facilitate such a control mechanism, the coffee roasting apparatus 100 may comprise a sensor arrangement 120 including a transmitter 122 and a receiver 124, which may be mounted in any suitable location of the compartment 110, e.g. in the roof or lid of the compartment 110. The operation of this sensor arrangement will be explained in more detail with the aid of FIG. 2.

Figure 2A:
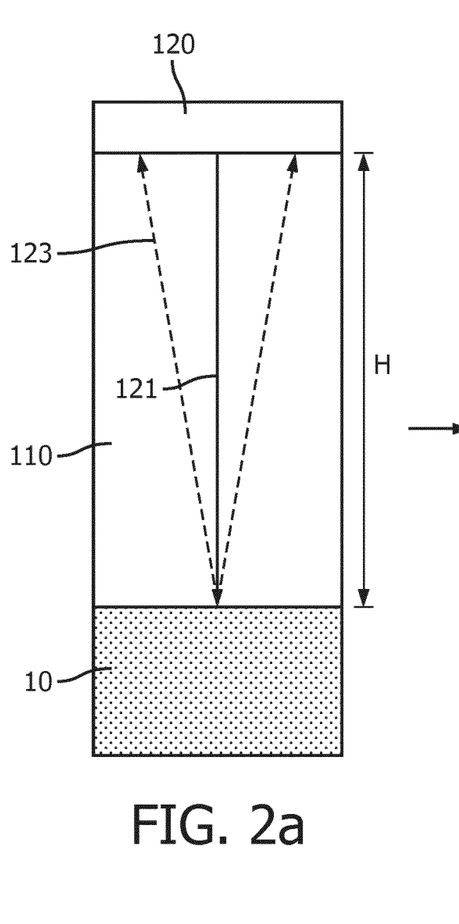
FIG. 2 schematically depicts an operating principle of the coffee roasting apparatus of FIG. 1.
Figure 2B:
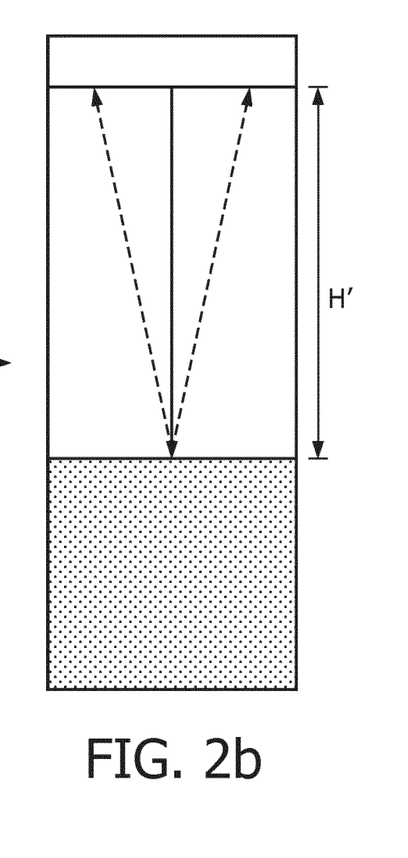

The transmitter 122 of the sensor arrangement 120 is typically arranged to transmit a signal 121 towards the coffee beans 10, with the receiver 124 of the sensor arrangement 120 typically arranged to detect a reflection 123 of the transmitted signal 121.

This reflection 123 is typically generated when the signal 121 has travelled the head space over the coffee beans 10 in the compartment 110, where the signal 121 is reflected by the coffee beans 10 and as such is an indication of the head space, i.e. the height H of the free volume, in the compartment 110 over the coffee beans 10.

An increase in the volume of coffee beans 10 in the compartment 110 during the roasting process caused by the expansion of the coffee beans 10 as indicated by the transition from the left panel to the right panel in FIG. 2 will lead to a reduction of the free volume or head space, i.e. a reduction of the height H to H', this reduction in head space can be determined from a reduction of the time-of-flight of the signal 121 and its reflection 123 from the transmitter 122 to the receiver 124: $H=(V*t)/2$ wherein V is the signal speed and t is the time-of-flight of the signal 121 and its reflection 123.

As the head space can be associated with a volume $V_{head}$ of the compartment 110, the total volume $V_{tot}$ of the compartment 110 can be expressed as $V_{tot}=V_{beans}+V_{head}$, wherein $V_{beans}$ is the volume portion of the compartment volume occupied by the coffee beans 10. As any change, i.e. reduction, in the measured head space volume $V_{head}$ is caused by a change in the coffee bean volume $V_{beans}$, the measured $V_{head}$ can be directly translated into the coffee bean volume: $V_{tot}-V_{head}=V_{beans}$, given that the total volume $V_{tot}$ of the compartment 110 is typically known. In other words, $H\sim V_{head}$, such that the determination of H can de directly translated into $V_{head}$.

Therefore, in an embodiment the sensor arrangement 120 is arranged to periodically determine the time-of-flight of the signal 121 and its reflection 123 such that the volume change in the coffee beans 10 can be monitored as a function of time by the coffee roasting apparatus 100: $\Delta H=H-H'=(V*\Delta t)/2$. Any suitable time period between subsequent head space determinations may be applied; for instance, the sensor arrangement 120 may be arranged to perform such periodic measurement at a frequency of once per second or less, e.g. a frequency in a range of 0.1-1.0 Hz, e.g. at a frequency of once per second or more, e.g. a frequency in a range of 1.0-50 or 60 Hz and so on.

The transmitter 122 and receiver 124 may cooperate in any suitable manner. For instance, the receiver 124 may be arranged to detect a single signal pulse transmitted by the transmitter 122 or may be arranged to detect a series of signal pulses transmitted by the transmitter 122, wherein t or $\Delta t$ is determined using an average time of flight of the series of pulses. The latter approach has the advantage that statistical outliers may be discarded, e.g. reflections not originating from the surface of the coffee beans 10, thereby potentially improving the accuracy of the time-of-flight determination.

The signal 121 may be any suitable signal, such as an optical signal, an acoustic signal or any other suitable type of electromagnetic signal. An optical signal such as a laser signal or an infrared signal affords more accurate determination of the coffee bean volume but may be relatively expensive to realize, whereas an acoustic signal such as an ultrasound signal can be produced more cheaply but may be less accurate than an optical signal. The signal 121 may have any suitable shape, such as a single pulse or a series of pulses per coffee bean volume determination.

In an embodiment, the sensor arrangement 120 is arranged to convert the determined time-of-flight of the signal 121 and its reflection 123 into the volume of the coffee beans 10 for instance as explained above. To this end, the sensor arrangement 120 may include a signal transducer and/or signal processor 126 performing the necessary signal conversions and/or calculations, resulting in the provision of a control signal to the controller 130 that is indicative of this volume or volume change. This control signal may be provided to the controller 130 in any suitable form, e.g. analogue or digital form.

Alternatively, the sensor arrangement may be arranged to simply forward the determined time-of-flight of the signal 121 and its reflection 123 to the controller 130, with the controller 130 being configured to translate the determined time-of-flight into a volume of the coffee beans 10 for instance as previously explained. To this end, the controller 130 may include the previously mentioned signal processor.

In yet another embodiment, the coffee roasting apparatus 100 may include a separate signal processor arranged to receive the time-of-flight data from the sensor arrangement 120, convert the received time-of-flight data into a volume of the coffee beans 10 for instance as previously explained, and provide the controller 130 with a control signal indicative of this volume.

The controller 130 may be adapted to control the heating arrangement in response to the time-of-flight determination by the sensor arrangement 120. In particular, the controller may be adapted to respond to an increase in the rate of volume change in the coffee beans 10 signalling the occurrence of the first cracking phase.

The controller 130 may be responsive to a user interface 150, which for instance may facilitate a user specifying the desired roasting degree of the coffee beans 10 in any suitable manner, e.g. using a dial, a series of buttons, a programmable display, which may be a touch-screen display and so on. Any suitable type of user interface 150 may be used for this purpose.

It will be understood that these embodiments are non-limiting examples of possible arrangements and that many other arrangements are equally suitable; for instance, even though the embodiment of the coffee roasting apparatus 100 as shown in FIG. 1 has been explained using a discrete controller 130, it is equally feasible that at least some of the discrete components form part of a single arrangement. For instance, the controller 130 may form part of the sensor arrangement 120 and so on.

Figure 3:
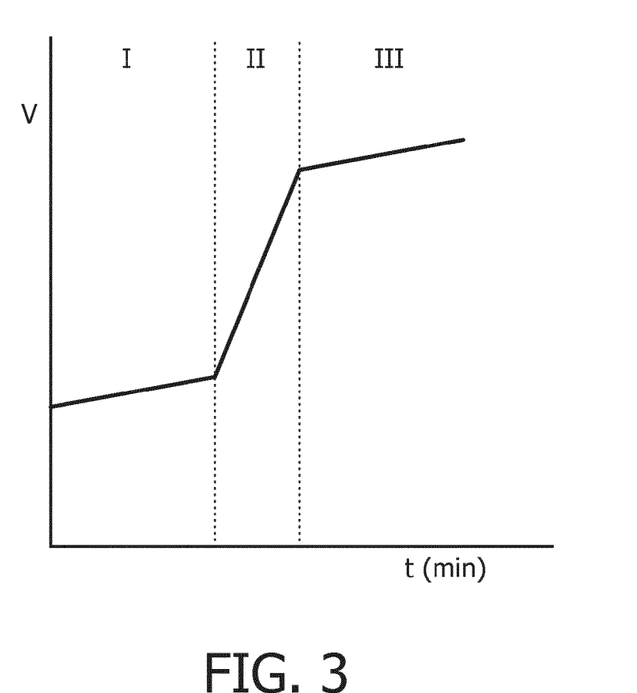
FIG. 3 schematically depicts a roasting profile of coffee beans in terms of volume changes in the coffee beans over time.

A typical coffee bean roasting profile is schematically depicted in FIG. 3, which schematically depicts the volume V of the coffee beans 10 as a function of the roasting time t. Three phases (labelled I, II and III) can be identified in the roasting process. During phase I, prior to the first cracking of the coffee beans 10, a modest gradual increase of the coffee bean volume is observed, which is typically less than 10%. During phase II, first cracking of the coffee beans 10 occurs, for instance due to pore forming within the coffee beans 10, which triggers a more rapid expansion of the coffee bean volume. During phase II, the coffee beans 10 may exhibit an increase in volume ranging from 40%-100% or more. Upon completion of phase II, the coffee beans 10 exhibit a more modest volume expansion during the final roasting phase III, e.g. less than 50%, e.g. in the range of 10-30%, with the rate of expansion being significantly smaller than during the first cracking phase II.

Figure 4:
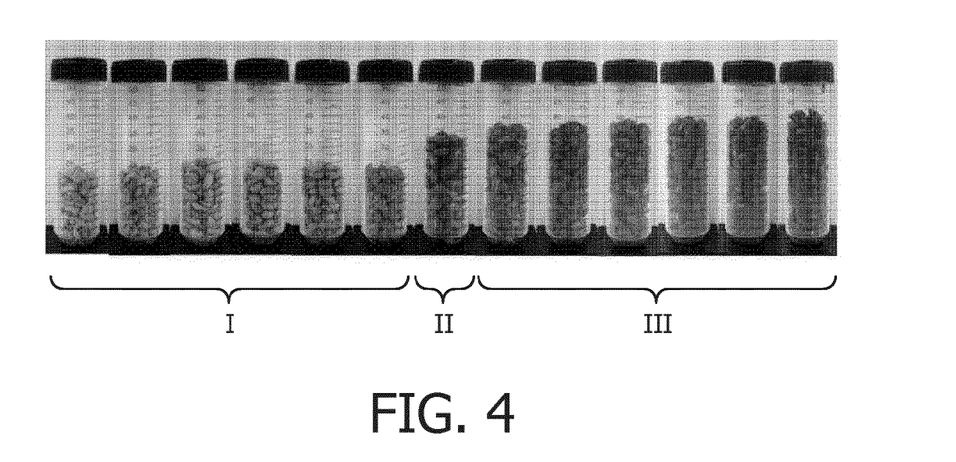
FIG. 4 depicts a series of images of various stages of a coffee roasting process.

These phases are further visualised in FIG. 4, which depicts a series of images of 14 g of Mandheling coffee beans captured at different points in time during the exposure of the beans to a typical thermal roasting process. The sudden increase in volume in the coffee beans during phase II, i.e. during the first cracking phase, is clearly evident.

Importantly, the inventors have realized that the point in time where the transition from phase I to phase II takes place can be unpredictable, i.e. subject to variation, whereas the completion of phase II and subsequent phase III is more predictable, i.e. less subject to variation. Therefore, the coffee roasting apparatus 100 may be configured to control the roasting process by monitoring the change in the volume of the coffee beans 10 in order to identify the occurrence of the first cracking phase II, thereby identifying the point in time from which the roasting process becomes more predictable.

In an embodiment, the coffee roasting apparatus 100 may be configured to monitor the rate of change of the volume of the coffee beans 10, with an increase in this rate indicating the start of the first cracking process and a subsequent reduction in this rate indicating the completion of the first cracking process. The rate of volume change may be determined in any suitable manner, e.g. by directly or indirectly determining the difference between subsequent volume determinations. An indirect determination may be the determination of the difference between the times-of-flight of subsequent signals 121 and their reflections 123, e.g. the difference between two subsequent measurements separated by a set time interval.

It should be understood that once the first cracking of the coffee beans 10 has been determined by way of detecting the sudden increase in (the rate of) volume change of the coffee beans 10 as previously explained, the coffee roasting apparatus 100 may be subsequently controlled by the controller 130 in any suitable manner. For instance, the controller 130 may remain responsive to the sensor arrangement 120 and may terminate the roasting process once the coffee beans 10 have increased in volume by a predetermined amount.

In an embodiment, the controller 130 may terminate the roasting process if the volume of the coffee beans 10, or the increase of this volume, exceeds a defined threshold, e.g. a predefined threshold or a user-defined threshold, in order to prevent the beans becoming too darkly roasted. For instance, the controller 130 may terminate the roasting process if, after completion of the first cracking stage, as for instance indicated by a reduction in the rate of volume expansion of the coffee beans 10, the volume of the coffee beans 10 has expanded by a predefined or user-defined amount to ensure that the coffee beans 10 have the desired degree of roasting. Alternatively, the controller 130 may terminate roasting process upon the initial volume of the coffee beans 10 having increased by a set amount, i.e. having increased to a target volume that is larger than the initial volume, as the amount of volume increase is indicative of the degree of roasting of the coffee beans 10.

In an embodiment, the coffee roasting apparatus 100 may be controlled by a combination of the aforementioned volume monitoring and at least one other parameter, such as time, bean color and/or temperature. This for instance may be advantageous to improve the control over the roasting process, in particular if the volume changes in the coffee beans 10 upon completion of the first cracking phase are modest and difficult to detect by monitoring volume change or volume change only. This for instance may be the case if the total volume of coffee beans 10 in the compartment 110 is relatively small.

In an example embodiment, the controller 130 may be adapted to engage the heating arrangement for a set period of time upon completion of the first cracking process as detected by the aforementioned volume changes in the coffee beans 10. The set period of time may correspond to a user-defined degree of roasting of the coffee beans 10, where a longer period of time typically corresponds to a darker roast of the coffee beans 10. To this end, the controller 130 may include or may have access to a look-up table or the like in which a time period is defined as a function of roasting degree. The controller 130 may further include a timer for controlling the heating arrangement in accordance with the set period of time. As it is well-known per se to control a heating arrangement of coffee roasting apparatus 100 using time as a control parameter, this will not be explained in further detail for the sake of brevity only. It is simply noted that the time control aspect of the aforementioned embodiment may be implemented in any suitable manner.

Figure 5:
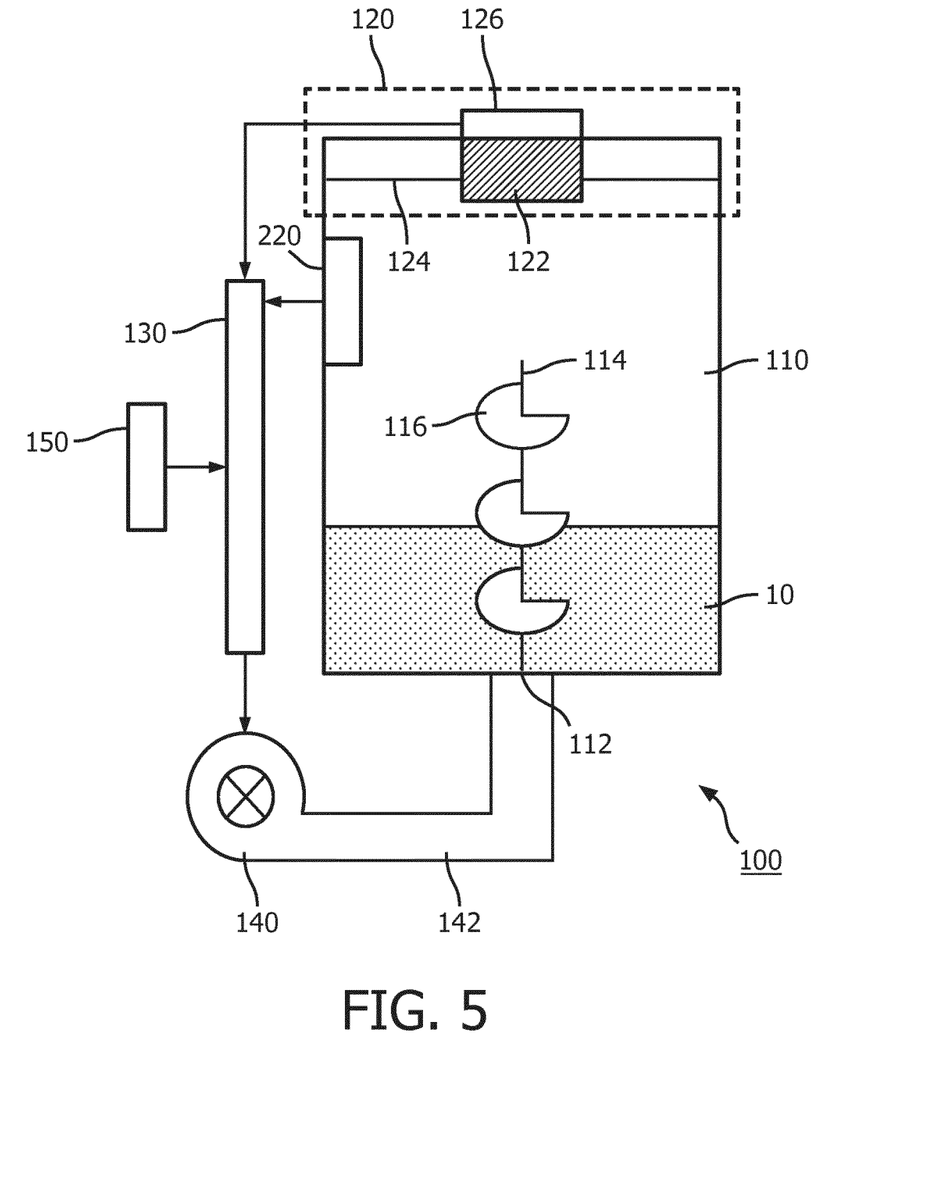
FIG. 5 schematically depicts a coffee roasting apparatus according to another embodiment.

In an example embodiment, the coffee roasting apparatus 100 may be further adapted to control the roasting process by determining the color of the coffee beans 10, for instance after completion of the first cracking phase of the coffee beans 10 as determined by the change in the volume of the coffee beans 10 as previously explained. To this end, a further sensor 220 may be present in the compartment 110 as schematically shown in FIG. 5, which further sensor 220 is arranged to determine the colour of the coffee beans 10 in the compartment 110. The further sensor 220 is communicatively coupled to the controller 130 such that the controller 130 can further control the heating arrangement of the coffee roasting apparatus 100 in response to the further sensor 220. As the process of coffee bean colour determination is well-known per se, this will not be explained in any further detail for the sake of brevity only. It is simply noted that any suitable coffee bean colour determination sensing arrangement may be used.

Figure 6:
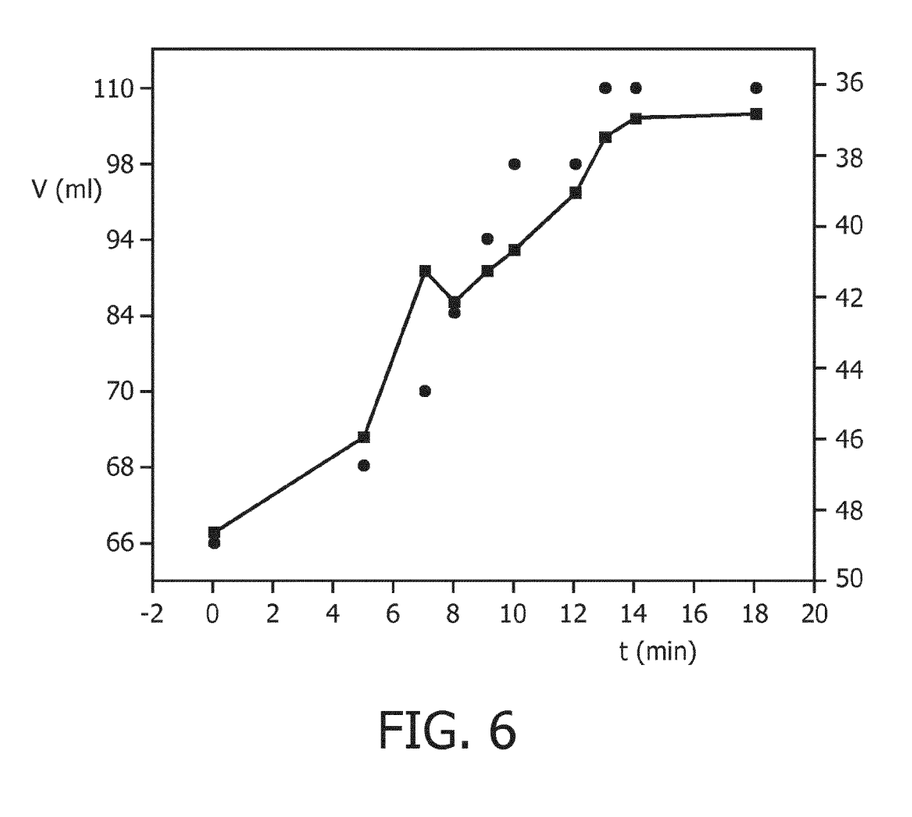
FIG. 6 schematically depicts an experimentally determined roasting profile of coffee beans in terms of volume and color changes in the coffee beans over time.

FIG. 6 shows an experimental graph showing changes in the volume V of Mandheling coffee beans (dots) and changes in the colour of these coffee beans (squares) as a function of roasting time. The volume scale (in ml) is depicted on the left-hand vertical axis and the colour scale (in Hunterlab colour coordinates) is depicted on the right-hand vertical axis of the graph. The horizontal axis (or x-axis) depicts the roasting time (in minutes). This graph clearly demonstrates that the roasting colour may be used as an auxiliary parameter to determine the progress of the roasting process of the coffee beans 10.

Figure 7:
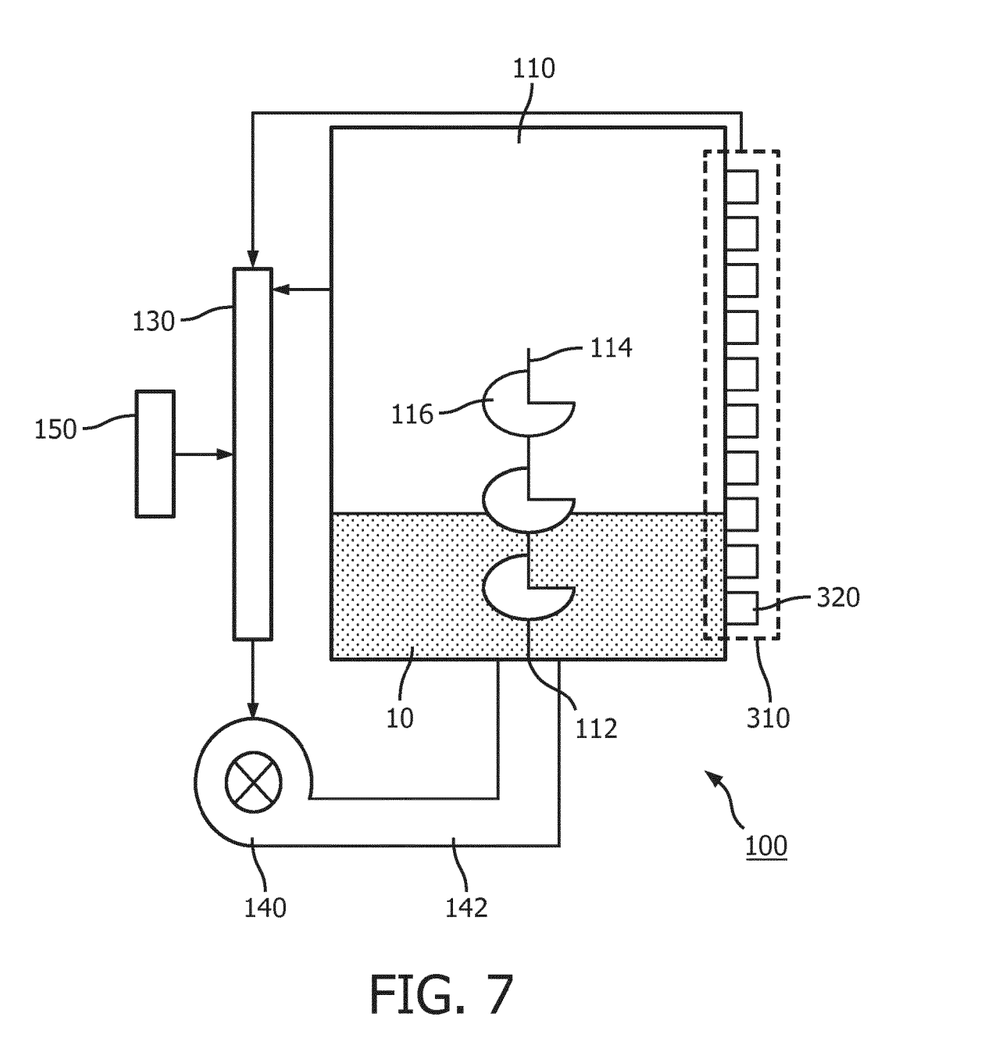
FIG. 7 schematically depicts a coffee roasting apparatus according to yet another embodiment.

At this point, it is noted that the volume change of the coffee beans 10 in the compartment 110 may be determined in any suitable manner, and that this determination is not limited to the time-of-flight measurement principle previously explained. An example alternative embodiment is schematically depicted in FIG. 7, in which the sensor arrangement 120 is replaced by a sensor arrangement 310 having a plurality of optical sensors 320 along a side wall of the compartment 110. Such optical sensors 320 may for instance be arranged to detect a light level at the height of the sensor 320 in the compartment 110, with the optical sensor 320 being covered by the volume of coffee beans 10 indicating a diminished light level.

The controller 130 may be arranged to detect which of the optical sensors 320 report such a diminished light level, which information may be translated into a volume of the coffee beans 10 due to the fact that the optical sensors 320 have a fixed (height) position along the side wall of the compartment 110. Alternatively, the sensor arrangement 310 may include a signal processor communicatively coupled to the optical sensors 320 to convert the sensor signals of the optical sensors 320 into a signal indicative of the volume of the coffee beans 10 and to forward this indicative signal to the controller 130.

The optical sensors 320 may be arranged to detect ambient light in the compartment 110. Alternatively, the coffee roasting apparatus 100 may further comprise a light source in the compartment 110 for generating light inside compartment 110 that can be detected by the optical sensors 320.

Other suitable volume change detection methods will be apparent to the skilled person, and it is noted that any of these suitable methods may be implemented in the coffee roasting apparatus 100 of the present invention.

In an embodiment, the coffee roasting apparatus 100 may further comprise a data storage element such as a RAM or Flash memory, look-up table or the like that is communicatively coupled to the controller 130 for storing a roasting profile of the coffee beans 10. The coffee roasting apparatus 100, e.g. by means of the controller 130 or by means of a separate signal processor, may be adapted to program a roasting profile as detected by the monitored volume changes of the coffee beans 10 into the data storage element. Such a stored roasting profile may be used during later roasts, e.g. to verify the desired roasting level by comparing the determined relative or absolute volume change against the stored roasting profile, to determine how far advanced the actual roasting process has progressed.

In an embodiment, the coffee roasting apparatus 100 may further comprise a data transmission device, e.g. a wireless or wired transmitter, for transmitting roasting data to an external source, e.g. over a wireless link and/or over the Internet or the like. This information for instance may be used to improve the embedded roasting profiles of future coffee roasting apparatuses.

The coffee roasting apparatus 100 may be integrated in a coffee brewing apparatus further comprising a coffee bean grinder and a coffee brewing stage. For instance, the coffee brewing apparatus may be arranged to automatically transfer a portion of the roasted coffee beans into the coffee bean grinder for grinding, after which the ground coffee is automatically transported into the coffee brewing stage for brewing a fresh cup of coffee. As such coffee brewing apparatuses are well-known per se, this will not be explained in further detail for reasons of brevity only. It should be understood that the particular embodiment of such a coffee brewing apparatus is not critical to the present invention and that any suitable arrangement of such coffee brewing apparatus may be contemplated.

Figure 8:
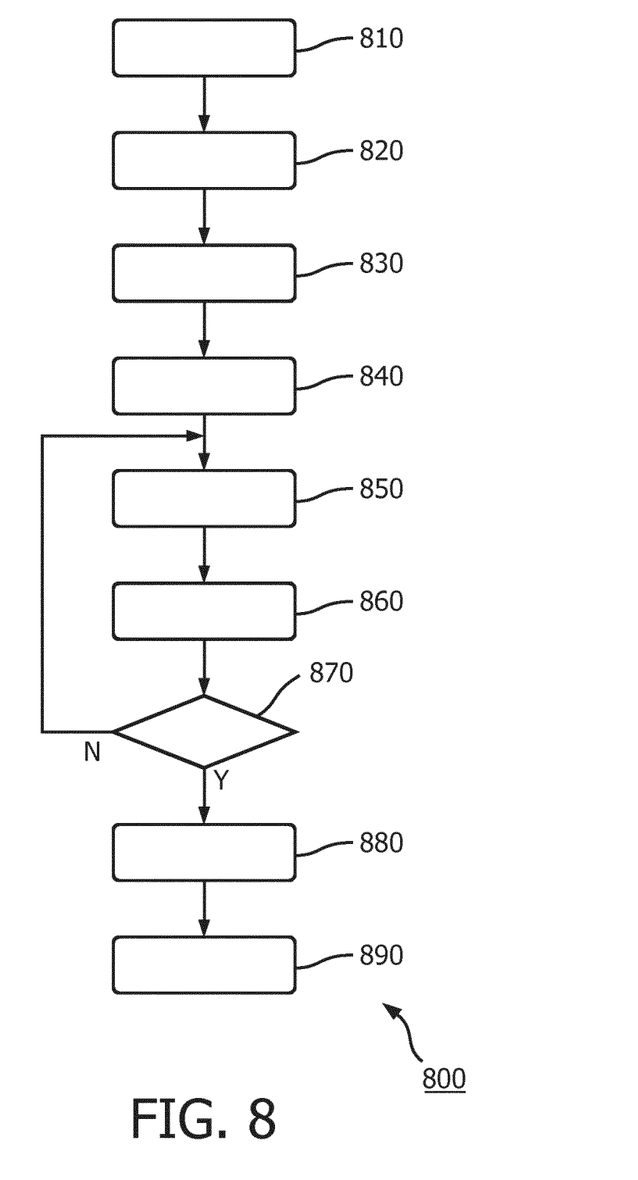
FIG. 8 schematically depicts a flowchart of a coffee roasting method according to an embodiment.

An example embodiment of the coffee brewing method 800 according to the present invention will now be explained in further detail with the aid of FIG. 8, which depicts a flowchart of this example embodiment. The method starts in step 810 for instance with the switching on of the coffee roasting apparatus 100 and/or the filling of the compartment 110 with the coffee beans 10 to be roasted. The method then proceeds to step 820 in which a user defines the desired roasting level of the coffee beans 10, for instance using the user interface 150.

In step 830, the sensor arrangement 120 (or any other suitable sensor arrangement, such as the sensor arrangement 310) determines the initial parameters of the coffee beans 10, such as the initial volume occupied by the coffee beans 10 in the compartment 110. It will be understood that although step 830 is shown as following step 820, it is equally feasible that step 830 is executed prior to or in parallel with step 820. The method then proceeds to step 840 in which the targeted volume of the coffee beans 10 corresponding to the desired roasting level as specified by the user in step 820 is determined. This for instance may be achieved by looking up a stored roasting profile and establishing the amount of volume increase required to achieve the desired roasting level. The targeted volume of the coffee beans 10 is typically based on the initial volume of the coffee beans 10 as determined in step 830.

Next, the coffee beans 10 are roasted in step 850 and the volume of the coffee beans 10 is monitored in step 860 during the roasting process of step 850. It is checked in step 870 if the actual volume of the coffee beans 10 as determined in step 860 corresponds to the target volume determined in step 840. If it is determined that the actual volume is smaller than the target volume, the method refers back to step 850 and the roasting of the coffee beans is continued. On the other hand, if it is determined that the actual volume of the coffee beans 10 as determined in step 860 corresponds to the target volume, the roasting process is terminated in step 880 after which the method is terminated in step 890, as the roasting process is complete.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A coffee roasting apparatus comprising:
   a compartment for holding coffee beans;
   a roasting element for roasting the coffee beans in said compartment; and
   a controller configured to control the roasting element as a function of a change in a volume of the coffee beans residing in the compartment, wherein the controller is configured to control the roasting element in response to a monitored rate of change of the volume exceeding a predefined threshold, said predefined threshold indicating first cracking of said coffee beans.

2. The coffee roasting apparatus of claim 1, wherein the controller is configured to control the roasting element in response to:
   an increase in the monitored rate of change of the volume indicative of the start of the first cracking of the coffee beans; and/or
   a decrease in the monitored rate of change of the volume indicative of the completion of the first cracking of the coffee beans.

3. The coffee roasting apparatus of claim 1, further comprising a sensor arrangement configured to determine an unoccupied volume of the compartment, wherein the controller is further configured to control the roasting element in response to the sensor arrangement.

4. The coffee roasting apparatus of claim 3, wherein the sensor arrangement comprises a sensor configured to transmit a signal into the compartment towards said coffee beans and to detect a reflection of said signal.

5. The coffee roasting apparatus of claim 4, wherein the signal is an optical signal or an acoustic signal.

6. The coffee roasting apparatus of claim 3, wherein the sensor arrangement is further configured to determine an initial volume occupied by said coffee beans and to monitor a change in said initial volume.

7. The coffee roasting apparatus of claim 1, wherein the controller is configured to enable the roasting element for a predefined time period upon the monitored rate of change of the volume indicative of said first cracking exceeding the predefined threshold.

8. The coffee roasting apparatus of claim 1, further comprising a data storage element configured to store a measured change in an unoccupied volume in the compartment as a function of time to define a roasting profile of a type of coffee beans, wherein:
   the controller is further configured to program said data storage element; and/or
   the controller is further configured to control the roasting element in accordance with the stored roasting profile in response to a user defining a degree of roasting for said type of coffee beans.

9. The coffee roasting apparatus of claim 1, wherein the controller is configured to disable the roasting element upon the monitored rate of change of the volume exceeding the predefined threshold.

10. A coffee brewing apparatus including the coffee roasting apparatus of claim 1.

11. A method of roasting coffee beans, the method comprising:
    heating the coffee beans to roast the coffee beans;
    monitoring a rate of change of volume of the coffee beans during said heating; and
    terminating said heating in response to said volume change rate exceeding a defined threshold, said defined threshold indicating first cracking of said coffee beans.

12. The method of claim 11, wherein the monitoring a rate of change of said volume comprises:
    monitoring an increase in the monitored rate of change of volume indicative of the start of first cracking of the coffee beans; and/or
    monitoring a decrease in the monitored rate of change of volume indicative of the completion of first cracking of the coffee beans.

13. The method of claim 11, wherein terminating said heating in response to said volume change exceeding a defined threshold comprises terminating said heating after a predefined period of time upon said volume change rate exceeding the defined threshold.

* * * * *